(12) United States Patent
Bates et al.

(10) Patent No.: US 6,174,318 B1
(45) Date of Patent: Jan. 16, 2001

(54) BASKET WITH ONE OR MORE MOVEABLE LEGS

(75) Inventors: James S. Bates, Bloomington; Tim E. Ward, Ellettsville, both of IN (US)

(73) Assignee: SciMed Life Systems, Inc., Maple Grove, MN (US)

( * ) Notice: Under 35 U.S.C. 154(b), the term of this patent shall be extended for 0 days.

(21) Appl. No.: 09/065,158

(22) Filed: Apr. 23, 1998

Related U.S. Application Data

(60) Provisional application No. 60/060,821, filed on Oct. 1, 1997.

(51) Int. Cl.[7] .................................................. A61B 17/22
(52) U.S. Cl. ......................... 606/127; 606/113; 606/200
(58) Field of Search .................... 606/127, 128, 606/113, 114, 115, 116, 200

(56) References Cited

U.S. PATENT DOCUMENTS

| | | | |
|---|---|---|---|
| 1,996,261 | * 4/1935 | Storz | 606/114 |
| 2,556,783 | 6/1951 | Wallace | 128/321 |
| 3,137,298 | 6/1964 | Glassman | 128/328 |
| 3,472,230 | 10/1969 | Fogarty . | |
| 3,739,784 | 6/1973 | Itoh | 128/320 |
| 3,828,790 | 8/1974 | Curtiss et al. | 128/320 |
| 3,955,578 | 5/1976 | Chamness et al. | 128/303.15 |
| 4,046,149 | * 9/1977 | Komiya | 128/328 |

(List continued on next page.)

FOREIGN PATENT DOCUMENTS

| | | |
|---|---|---|
| 56865/86 | 4/1986 | (AU) . |
| 2804058 A1 | 8/1978 | (DE) . |
| 2821048 | 11/1979 | (DE) . |
| 3213223 A1 | 10/1983 | (DE) . |
| 3407708 A1 | 9/1985 | (DE) . |
| 3522649 A1 | 1/1986 | (DE) . |
| 8707515 U1 | 9/1987 | (DE) . |
| 8707516 U1 | 10/1987 | (DE) . |
| 3620385 C1 | 1/1988 | (DE) . |
| 3633527 A1 | 4/1988 | (DE) . |
| 3633527A1 | 4/1988 | (DE) . |
| 4025799 A1 | 2/1992 | (DE) . |
| 32 13 223 A1 | 10/1993 | (DE) . |
| 0160870 A2 | 11/1985 | (EP) . |
| 0 195 444 | 9/1986 | (EP) . |
| 0195444 A2 | 9/1986 | (EP) . |
| 0 428 998 A1 | 5/1991 | (EP) . |
| 0428998 A1 | 5/1991 | (EP) . |
| 0 737 450 A1 | 10/1996 | (EP) . |
| 2694687 A1 | 2/1994 | (FR) . |
| 2 020 557A | 11/1979 | (GB) . |
| 3-205043 | 9/1991 | (JP) . |
| WO 91/11209 | 8/1991 | (WO) . |
| 92/05828 | 4/1992 | (WO) . |
| 92/16153 | 10/1992 | (WO) . |
| WO 94/24946 | 11/1994 | (WO) . |
| 95/05129 | 2/1995 | (WO) . |
| WO 96/01591 | 1/1996 | (WO) . |

OTHER PUBLICATIONS

Copy of International Search Report for PCT/US98/20556.
Vorwerk, Dierk et al., "Percutaneous Embolectomy: In Vitro Investigations of the Self–expanding Tulip Sheath", Radiology (1992) 182: 415–418.
Vorwerk, Dierk et al., "Percutaneous Balloon Embolectomy with a Self–expanding Tulip Sheath: In Vitro Experiments", Radiology (1995) 197: 153–156.

*Primary Examiner*—Michael Buiz
*Assistant Examiner*—Lien Ngo
(74) *Attorney, Agent, or Firm*—Testa, Hurwitz & Thibeault, LLP

(57) ABSTRACT

A medical retrieval device includes a basket with three or more legs. The device can be used to retrieve material from a body such as stones. At least one of the legs of the basket is moveable independently from at least one of the other legs. This independent movability allows material to be captured more readily and easily. A distal end of the basket can be non-perforated.

9 Claims, 11 Drawing Sheets

U.S. PATENT DOCUMENTS

| | | | |
|---|---|---|---|
| 4,046,150 | 9/1977 | Schwartz et al. | 128/328 |
| 4,198,960 | 4/1980 | Utsugi | 128/6 |
| 4,234,040 | 1/1981 | Beecher | 128/328 |
| 4,299,225 | 11/1981 | Glassman | 128/328 |
| 4,326,530 | 4/1982 | Fleury, Jr. | 128/303.14 |
| 4,347,846 | 9/1982 | Dormia | 128/328 |
| 4,425,908 | 1/1984 | Simon | 128/1 R |
| 4,447,227 | 5/1984 | Kotsanis | 604/95 |
| 4,557,255 | 12/1985 | Goodman | 128/7 |
| 4,590,938 | 5/1986 | Segura et al. | 128/328 |
| 4,611,594 | 9/1986 | Grayhack et al. | 128/328 |
| 4,612,931 | 9/1986 | Dormia | 128/328 |
| 4,625,726 | 12/1986 | Duthoy | 128/328 |
| 4,650,466 | 3/1987 | Luther | 604/95 |
| 4,682,599 | 7/1987 | Konomura | 128/328 |
| 4,691,705 | 9/1987 | Okada | 128/328 |
| 4,699,147 | 10/1987 | Chilson et al. | 128/642 |
| 4,706,671 | 11/1987 | Weinrib | 128/348.1 |
| 4,718,419 | 1/1988 | Okada | 128/303.15 |
| 4,723,549 | 2/1988 | Wholey et al. | 128/344 |
| 4,728,319 | 3/1988 | Masch | 604/22 |
| 4,790,812 | 12/1988 | Hawkins, Jr. et al. | 604/22 |
| 4,790,813 | 12/1988 | Kensey | 604/22 |
| 4,794,928 | 1/1989 | Kletschka | 128/344 |
| 4,807,626 | 2/1989 | McGirr | 128/328 |
| 4,873,978 | 10/1989 | Ginsburg | 128/345 |
| 4,893,621 | 1/1990 | Heyman | 606/127 |
| 4,907,572 | 3/1990 | Borodulin et al. | 606/128 |
| 4,926,858 | 5/1990 | Gifford, III et al. | 606/159 |
| 4,927,426 | 5/1990 | Dretler | 606/128 |
| 4,927,427 | 5/1990 | Kriauciunas et al. | 606/128 |
| 4,994,079 | 2/1991 | Genese et al. | 606/206 |
| 4,998,539 | 3/1991 | Delsanti | 128/898 |
| 5,011,488 | 4/1991 | Ginsburg | 606/159 |
| 5,030,201 | 7/1991 | Palestrant | 604/22 |
| 5,041,093 | 8/1991 | Chu | 604/104 |
| 5,053,008 | 10/1991 | Bajaj | 604/104 |
| 5,057,114 | 10/1991 | Wittich et al. | 606/127 |
| 5,064,428 | 11/1991 | Cope et al. | 606/127 |
| 5,071,407 | 12/1991 | Termin et al. | 604/104 |
| 5,084,054 | 1/1992 | Bencini et al. | 606/113 |
| 5,100,423 | 3/1992 | Fearnot | 606/159 |
| 5,102,415 | 4/1992 | Guenther et al. | 604/159 |
| 5,171,233 | 12/1992 | Amplatz et al. | 604/281 |
| 5,176,688 | 1/1993 | Narayan et al. | 606/128 |
| 5,192,286 | 3/1993 | Phan et al. | 606/127 |
| 5,290,294 | 3/1994 | Cox et al. | 606/108 |
| 5,311,858 | 5/1994 | Adair | 128/4 |
| 5,329,942 | 7/1994 | Gunther et al. | 128/898 |
| 5,330,482 | 7/1994 | Gibbs et al. | 606/113 |
| 5,345,936 | 9/1994 | Pomeranz et al. | 128/642 |
| 5,354,310 | 10/1994 | Garnic et al. | 606/198 |
| 5,376,100 | 12/1994 | Lefebvre | 606/180 |
| 5,421,832 | 6/1995 | Lefebvre | 604/53 |
| 5,471,982 | 12/1995 | Edwards et al. | 128/642 |
| 5,486,183 * | 1/1996 | Middleman et al. | 606/113 |
| 5,496,330 | 3/1996 | Bates et al. | 606/127 |
| 5,499,981 | 3/1996 | Kordis | 606/41 |
| 5,549,626 | 8/1996 | Miller et al. | 606/200 |
| 5,562,678 * | 10/1996 | Booker | 606/113 |
| 5,658,296 | 8/1997 | Bates et al. | 606/127 |
| 5,693,069 | 12/1997 | Shallman | 606/205 |
| 5,891,153 * | 4/1999 | Peteson | 606/107 |

* cited by examiner

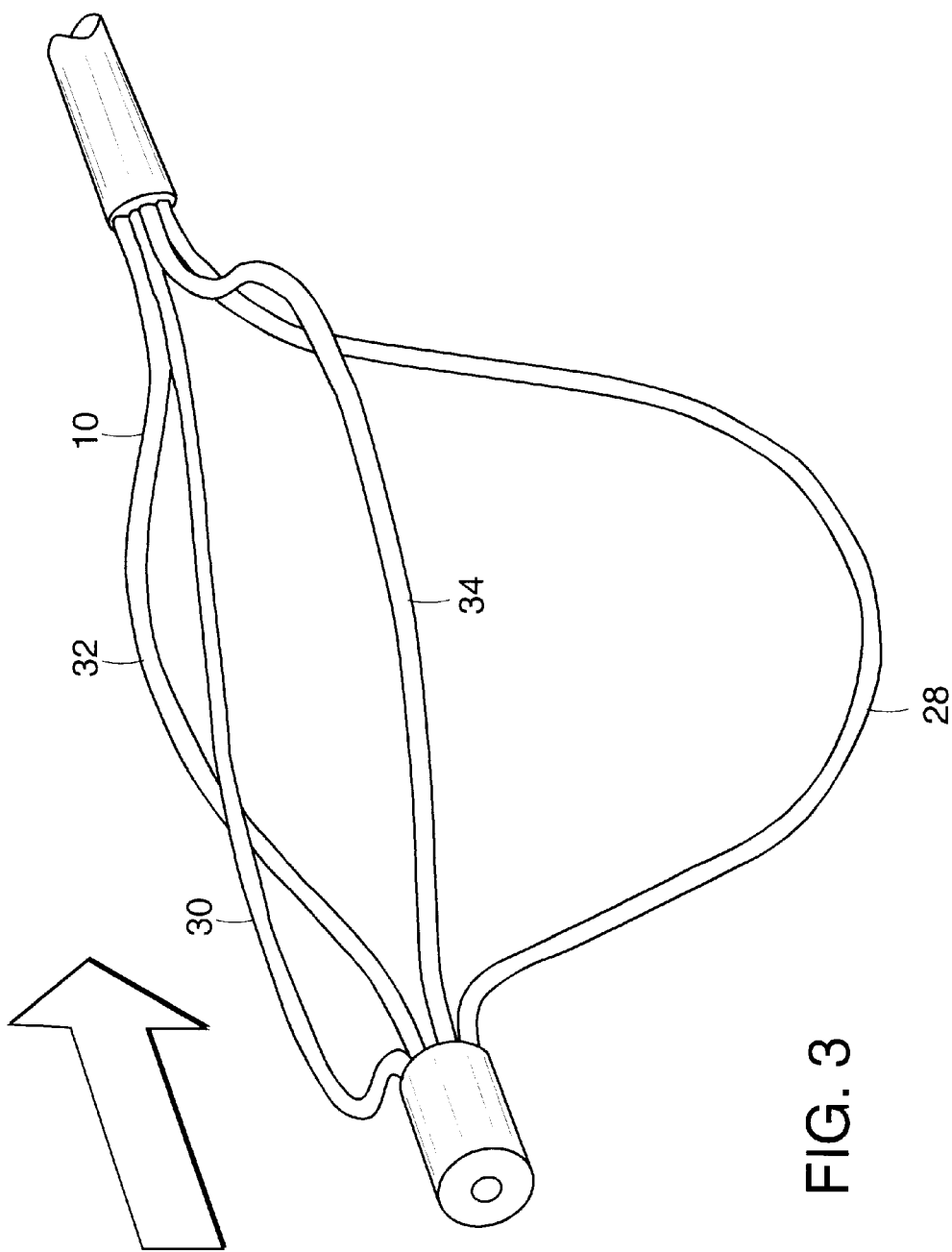

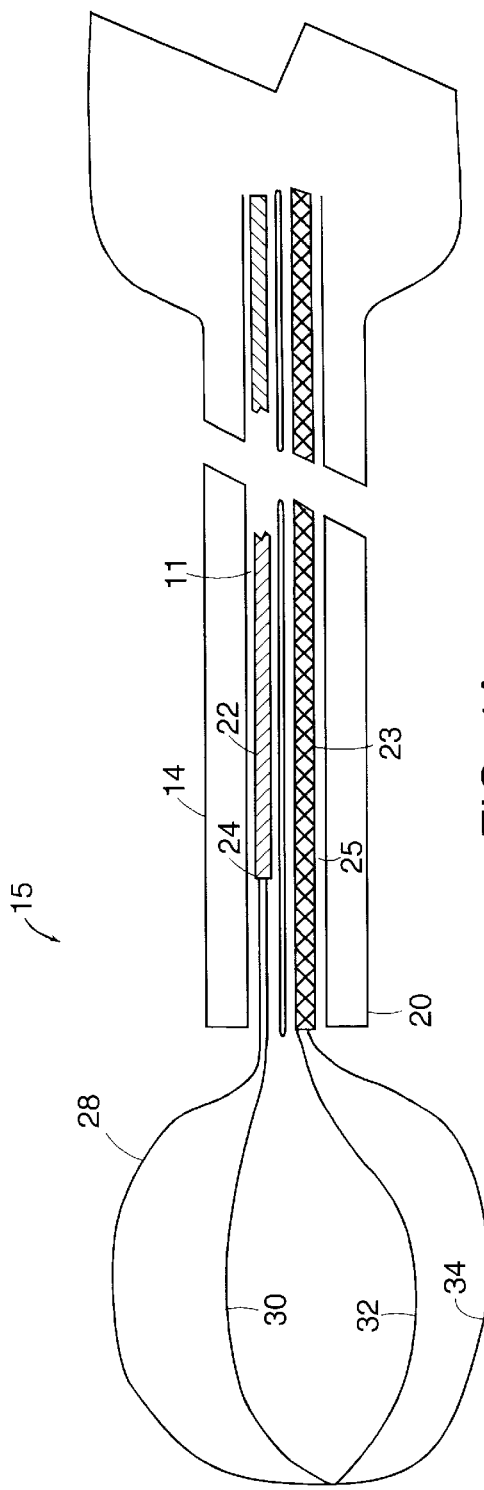
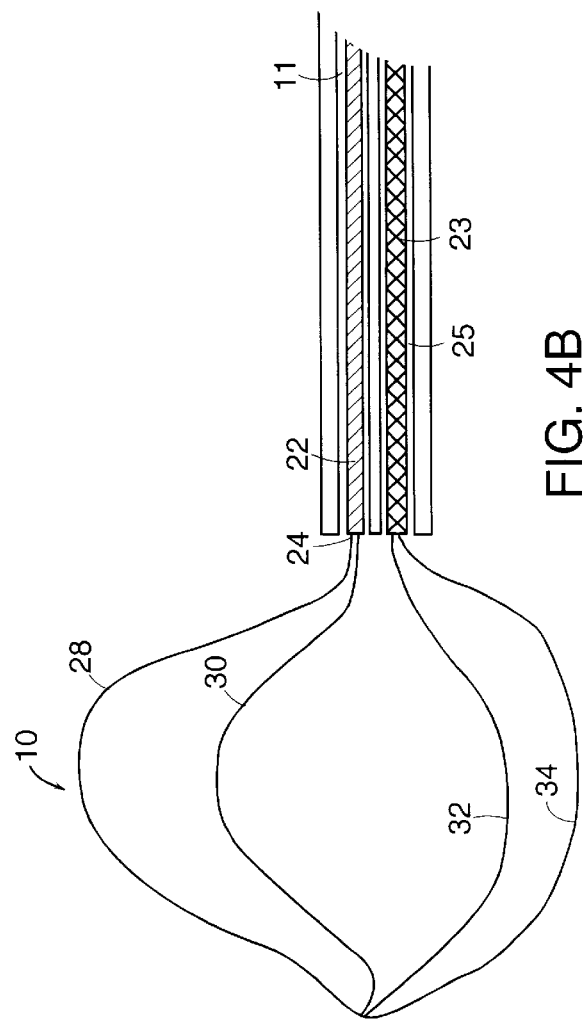
FIG. 4A
FIG. 4B

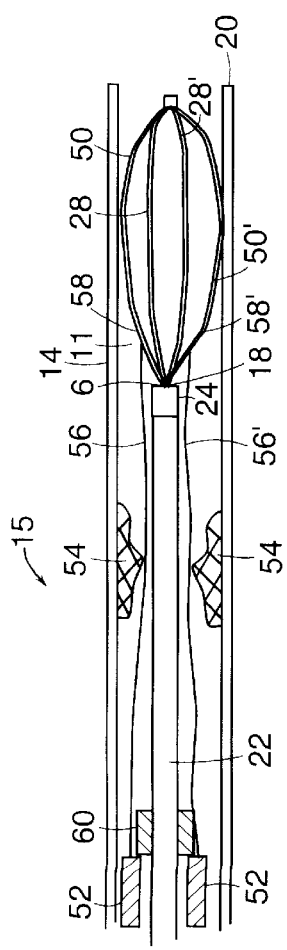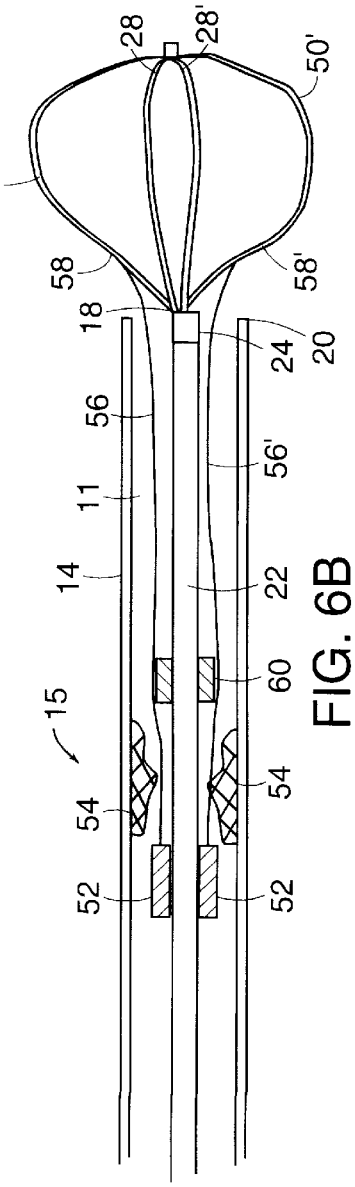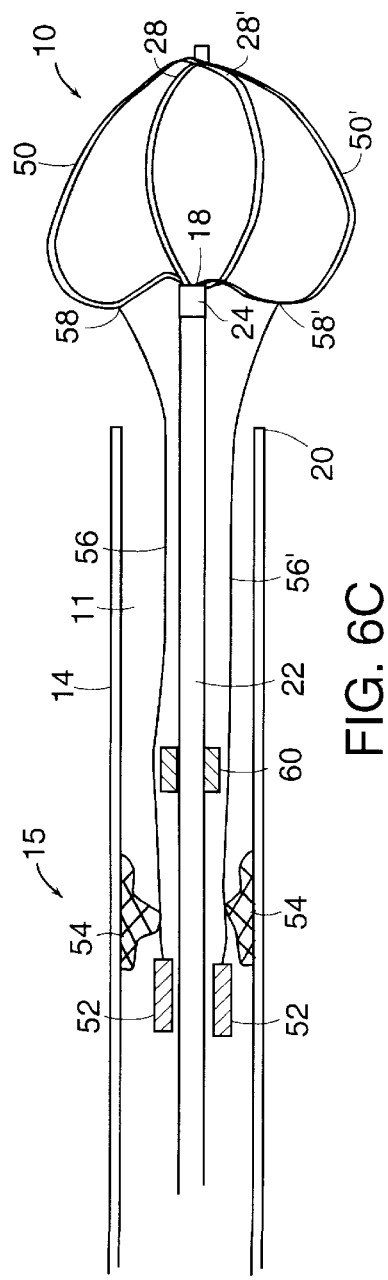

BASKET WITH ONE OR MORE MOVEABLE LEGS

CROSS-REFERENCE TO RELATED APPLICATIONS

This is based on and claims priority to provisional U.S. patent application Ser. No. 60/060,821 which was filed on Oct. 1, 1997. Also, the entirety of U.S. Pat. No. 4,590,938 is incorporated herein by reference.

TECHNICAL FIELD

The invention generally relates to medical retrieval devices for retrieving material from within a body. More particularly, the invention relates to such a device that has a basket at its distal end with one or more legs that are actuateable independent of the other legs for maneuvering the basket around the material (e.g., a stone of some kind) to enhance the basket's ability to capture the material.

BACKGROUND INFORMATION

Baskets are used to retrieve biological material from the body. Baskets are used, for example, to retrieve stones from the urinary tract (e.g., ureteral stones) or stones from the biliary tree (e.g., bile duct stones). Baskets may or may not be used through a catheter, an endoscope, or a laparoscope.

Existing retrieval baskets generally consist of legs, and the diameter and overall shape of the basket is defined by the number, flexibility, shape, and length of the legs. The legs generally are equal and fixed in length, providing overall symmetry to the basket shape. The legs of the basket typically are joined at the tip of the basket and at the base of the basket closest to the sheath. The legs can be joined with solder, by welding the legs together, or by some type of mechanical mechanism. At the basket base, the joined legs typically also are attached to a shaft, wire, or coil. The shaft can be moved back and forth within the sheath or catheter by an actuation device such as a proximal handle with a back-and-forth hand-activated slider. Alternatively, the sheath can be moveable back and forth to expose and cover the basket. In any case, the basket is exposed and expanded fully, within the sheath and collapsed fully, or somewhere in between those two extreme positions, and the legs generally all move in a collective manner as they are joined at both the tip and base to form the basket.

SUMMARY OF THE INVENTION

The invention features a medical retrieval device that has a basket with one or more legs that are actuateable or moveable independent from the other legs to facilitate the capture of material (e.g., a stone) from within the body and to improve retention of the captured material in the basket. For example, one leg of a four leg basket can be independently moveable, or two of the four legs can be actuated together independent of the other two legs, or three legs of a five leg basket can be moveable together independent of the fourth and fifth legs. Baskets according to the invention can be tilted, maneuvered, and/or steered to achieve capture and release of the material. A basket of the invention also allows improved dilation or opening force to expand a tract in which the basket is placed. According to the invention, the shape and size of the distance between at least one pair of basket legs is adjustable by individual action of one or more legs. That is, when the basket is maneuvered to capture a stone, at least one leg can be actuated independently to adjust the distance between the basket legs. Once the stone is captured, the independently actuateable leg(s) can be moved again alone and/or with the other legs to retain the stone. In one embodiment, the distal end of the basket is non-perforated, which can aid in retaining the captured material within the basket.

In one aspect, the invention relates to a medical retrieval device that comprises a proximal handle, a sheath, and a basket. The sheath extends from the handle and has at least one lumen therewithin. The sheath has a distal end away from the handle and a proximal end nearer the handle. The basket is moveable within the lumen relative to the sheath between a collapsed position within the lumen of the sheath and an extended position in which the basket extends from the distal end of the sheath and assumes a three-dimensional shape out of the lumen of the sheath. The basket comprises at least three legs, and at least one of the legs is moveable independently from at least one of the other legs. For example, two of the legs can be moved together independent from the other basket legs, or one leg could be moveable independent of all of the other legs.

Embodiments according to this aspect of the invention can include various features. For example, at least one of the legs can be coupled to a first elongate member extending within the lumen of the sheath to the handle, and at least one other different one of the legs can be coupled to a second elongate member extending within the lumen of the sheath to the handle, such that independent movement of the first elongate member within the sheath causes independent movement of the leg coupled thereto and independent movement of the second elongate member within the sheath causes independent movement of the leg coupled thereto. Also, at least one of the legs can include an inner surface which has at least a portion that is roughened. The basket shape can have a distal end which is non-perforated.

In another aspect, the invention involves a device of the type described above with a handle, sheath and basket. This device also includes first and second elongate members, a ring, and a stop. The first elongate member is disposed and moveable within the lumen of the sheath, and it is attached at one end to a base of the basket. The ring encircles the first elongate member, and it is disposed and moveable within the lumen of the sheath. The second elongate member is moveable within the lumen of the sheath, and it is attached at one end to the ring and at the other end to at least one of the legs. The stop is located within the lumen of the sheath for contact by the ring to prevent the second elongate member from advancing beyond a predetermined distance within the lumen such that further movement by the first elongate member within the lumen toward the distal end of the sheath causes the basket to "mushroom" or otherwise alter its shape.

In still another aspect, the invention relates to a medical retrieval device that comprises a proximal handle, a sheath, and a basket, and the sheath has a plurality of lumens therewithin. The sheath has a distal end away from the handle and a proximal end nearer the handle. The basket is moveable between a collapsed position and an extended position, and the basket comprises at least three legs with each leg being disposed and moveable within a different one of the lumens. The basket takes a three-dimensional shape when all legs are extended out of the distal end of the sheath. The basket shape has a distal end which is non-perforated, and at least one of the legs is moveable independently from at least one of the other legs.

Embodiments according to this aspect of the invention can include various features. For example, each of the legs can be coupled to an elongate member extending within each of the lumens to the handle, and at least one of the elongate members can be moveable independently from at least one of the other elongate members, such that independent movement of at least one of the elongate members within the sheath causes independent movement of the leg coupled thereto. Also, at least one of the legs can include an inner surface which has at least a portion that is roughened to facilitate purchase on the item to be retrieved.

In yet another aspect, the invention relates to a method for retrieving material from a body. The method comprises inserting a medical retrieval device (such as a device described above) into a body, placing the basket in the extended position, maneuvering the basket to surround the material by moving at least one of the legs independently from at least one of the other legs, drawing all of the legs back into the lumen to grasp the material with the legs of the basket, and withdrawing the device from the body to remove the grasped material from the body.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also the drawings are not necessarily to scale, emphasis instead generally being placed upon illustrating the principles of the invention.

FIG. 3 shows another basket which is similar to the basket of FIG. 2 with the basket in the extended open position.

FIG. 4A is a plan view of one embodiment of a basket according to the invention, with the basket in an extended closed position and having a pair of actuateable legs, two elongate members, and a single lumen within the sheath.

FIG. 4B shows the basket of FIG. 4A in an extended open position.

FIGS. 6A–6C show another embodiment of a medical retrieval device according to the invention, and the device in use.

DESCRIPTION

Figure 1A:
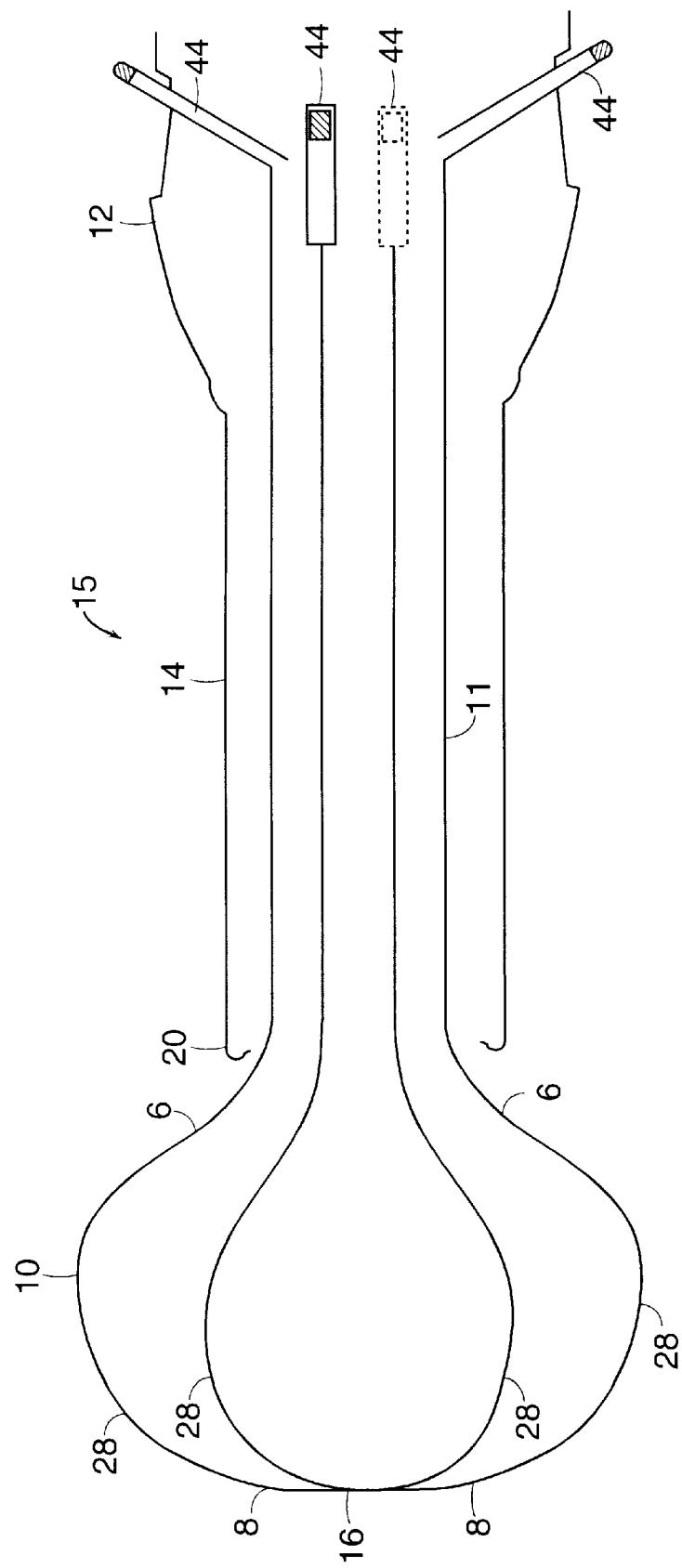
FIG. 1A is a plan view of a medical retrieval device with legs that extend along the entire length of the sheath to the actuating handle.

Referring to FIG. 1A, a medical retrieval device 15 for retrieving biological material or foreign material from a body comprises a distal basket 10, a proximal handle 12, and a sheath 14 disposed therebetween. The sheath 14 has at least one lumen 11 therewithin. The basket 10 is moveable relative to the sheath between a collapsed position and an extended position, and it is shown extended in a closed position in FIG. 1A. In one embodiment, the basket 10 comprises a non-perforated tip 16 and a plurality of legs 28. Each of the legs 28 having a distal end 8 at the tip of the basket 10 and a proximal end 6 at the base of the basket 10. The distal end 8 of each leg meets at the tip 16, and the proximal end 6 of each leg extends at least to a distal end 20 of the sheath 14.

In the disclosed embodiment, the basket legs are made of metal wire, although a variety of other materials can be used to form the legs such as polymers. The sheath 14 typically is made of a biocompatible material such as a plastic.

With continued reference to FIG. 1A, one or more lumens 11 extend within and are defined by the sheath 14. In some embodiments, there is one lumen 11, and the proximal end 6 of each of the legs 28 extends into that lumen 11. In one embodiment, each basket leg 28 runs individually down the entire length of the sheath 14. By keeping each leg 28 independent as it extends from the basket tip 16 to the actuating handle 12, several modes of operation can be achieved. For example, all basket legs can be actuated equally together, or an independent actuation of a leg can be performed. By actuating only one or two legs the basket can be maneuvered or tilted in a body tract, thereby increasing the ability to manipulate, capture or release a stone.

Figure 1B:
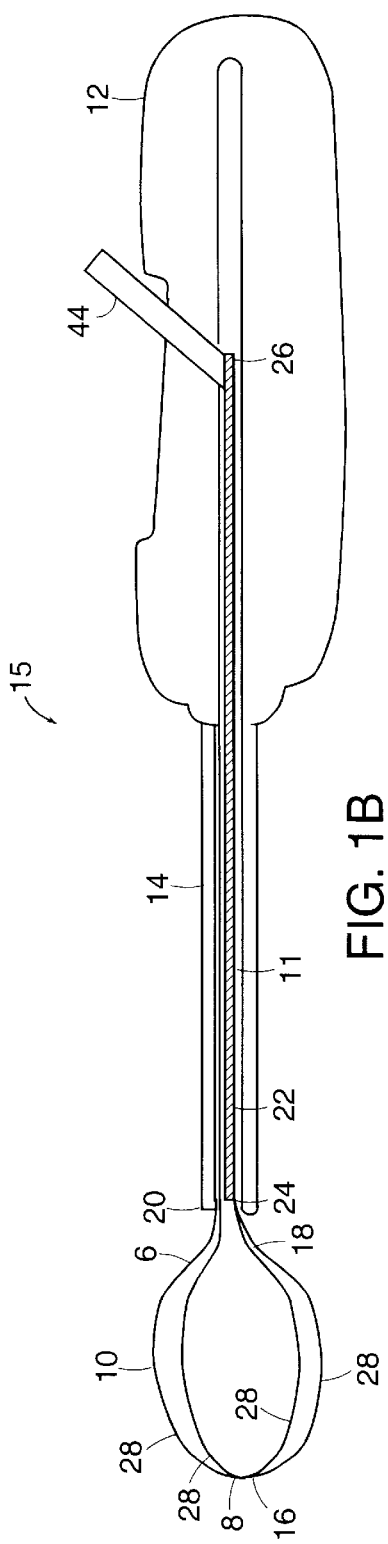
FIG. 1B is a plan view of a medical retrieval device with at least one elongate member in the lumen of the sheath.

Referring to FIG. 1B in another embodiment of the invention, one or more elongate members 22 which are disposed in the lumen(s) 11 are operably attached to the proximal end 6 of one or more of the basket legs 28. The remaining legs may be attached to another elongate member or to a fixed point such as the end 20 of sheath 14. The elongate member(s) 22 are slideably moveable within the lumen 11 of the sheath 14, and they can be shafts, wires, coils, cables, or constructed in a variety of other ways. In the disclosed embodiment, the member(s) 22 generally are single-strand metal wires. The proximal end 24 of the elongate member 22 may be attached to an actuating device such as a slider 44 in the handle 12. Advancing or retracting the slider 44 advances or retracts one or more basket legs 28 attached to a distal end 24 of the elongate member(s) 22. The device 15 could alternately be constructed to achieve movement of the sheath 14 over the member(s) 22, but that is not shown.

Figure 1C:
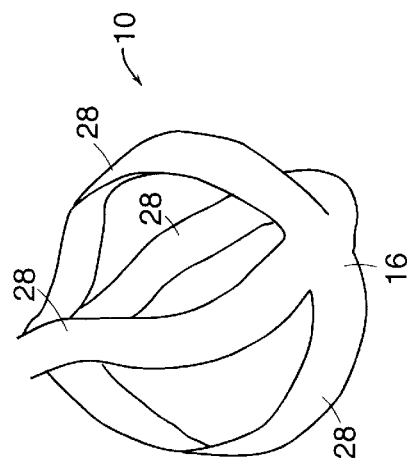
FIG. 1C is an end view of a non-perforated tip of a basket in accordance with the invention.

In a disclosed embodiment, the tip 16 is non-perforated as shown in FIG. 1C. That is, the tip 16 has no openings in it. Instead of being flat, as shown in FIG. 1C, the tip 16 of the basket can have a button, knob, or other protrusion, as shown for example in FIG. 3, which gathers the distal ends of the basket legs and holds them together.

Figure 1D:
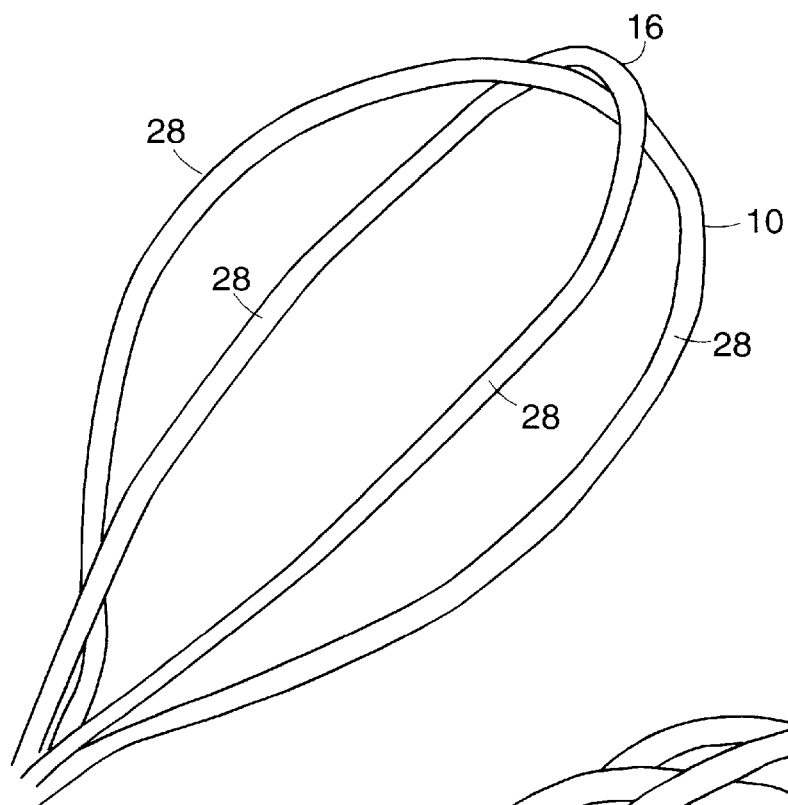
FIG. 1D shows another basket of the invention formed by at least two loops, the loops being unattached at the point where the loops intersect at the distal end of the basket.
Figure 1E:
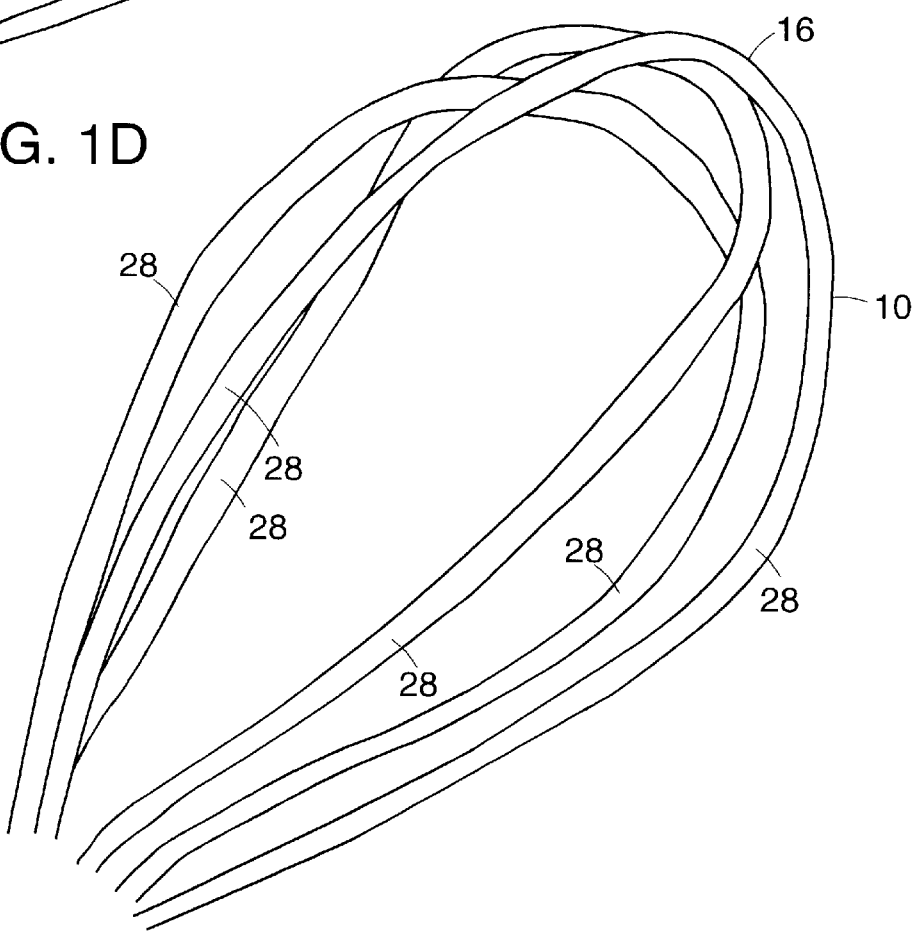
FIG. 1E shows another basket of the invention similar to FIG. 1C where the basket is formed by a plurality of loops, the loops being unattached where the loops intersect at the distal end of the basket.

Referring to FIGS. 1D and 1E, in an alternative embodiment of the invention, the basket has two or more separate loops that intersect at the distal end of the basket. The loops are loose, that is the loops are not joined, secured or attached to each other at the distal end of the basket. The width of the space between the loops at the distal end of the basket is changeable when an unsecured loop at the distal end of the basket is extended.

While four-leg baskets are shown and described with reference to FIGS. 1A–D and other drawings, it should be understood that any number of legs is possible. In general, three or more legs are required to form a basket as illustrated in FIG. 1E, three loops of the basket form a 6-leg basket.

Figure 2:
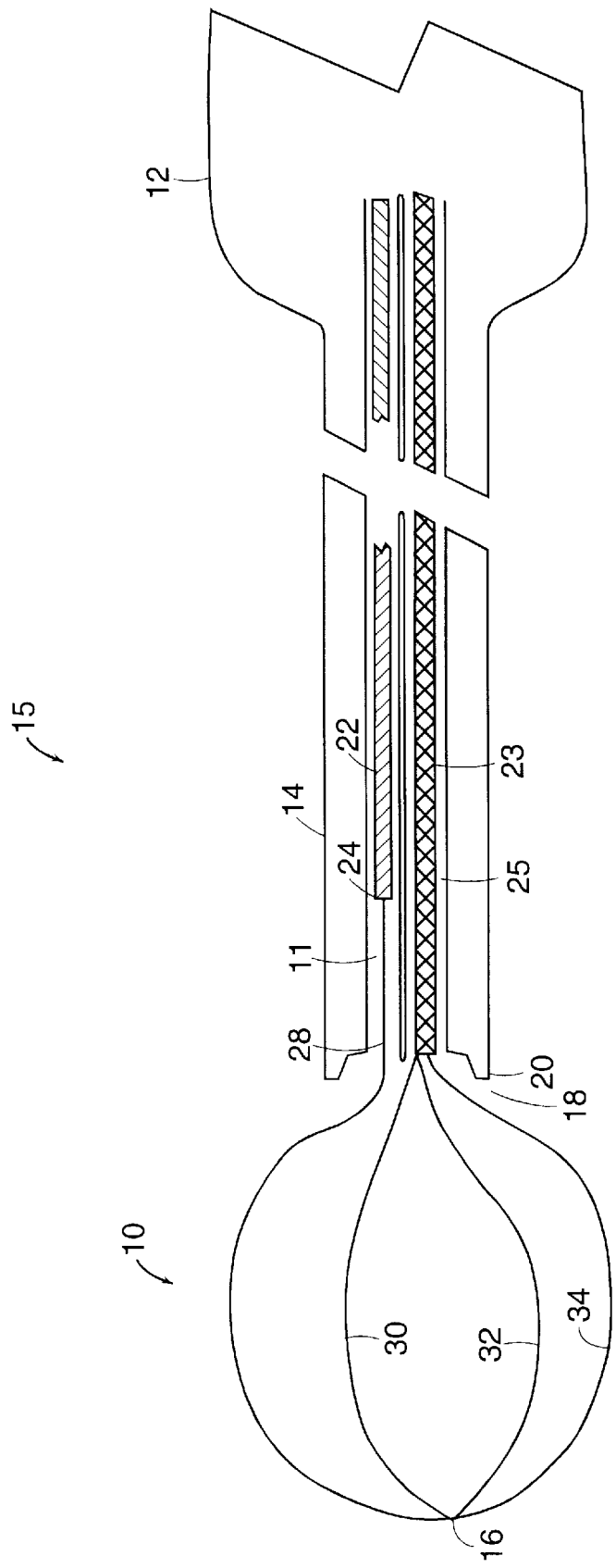
FIG. 2 is a plan view of one embodiment of a device according to the invention, with the basket of the device in an extended closed position and having one actuateable leg, two elongate members, and two lumens in the sheath.

In one embodiment, as shown in FIG. 2 with the basket 10 in an extended, closed position, one of the legs (28) of the basket 10 is attached to the distal end 24 of a first elongate member 22 within a first lumen 11 of the sheath 14, and the three other legs (30, 32, 34) of the basket 10 are attached at the base 18 of basket 10 to a second elongate member 23 in a second lumen 25. Referring to FIG. 3, advancing the first elongate member 22 in a direction towards the distal end 20 of the sheath 14 causes the leg 28 to extend further from sheath 14 than the other basket legs 30, 32 and 34, thereby forcing leg 28 to bend outward and altering or tilting the shape of the expanded basket 10 into an extended, open position.

Referring to FIG. 4A, in another embodiment, two of the legs (28, 30) are attached to the distal end 24 of the first elongate member 22, and the two remaining legs (32, 34) are attached to the distal end of the second elongate member 23. The two elongate members 22 and 23 are enclosed within the first lumen 11 and the second lumen 25 of sheath 14, respectively. When the first elongate member 22 is advanced toward the distal end 20 of the sheath 14, the legs 28 and 30 hyperextend from the end of the sheath 14 and thereby cause the basket 10 to move and alter its symmetrical shape. In FIG. 4B, the basket 10 is shown with the legs 28, 30 hyperextended such that the basket 10 assumes a tilted shape in the extended, open position.

Figure 4C:
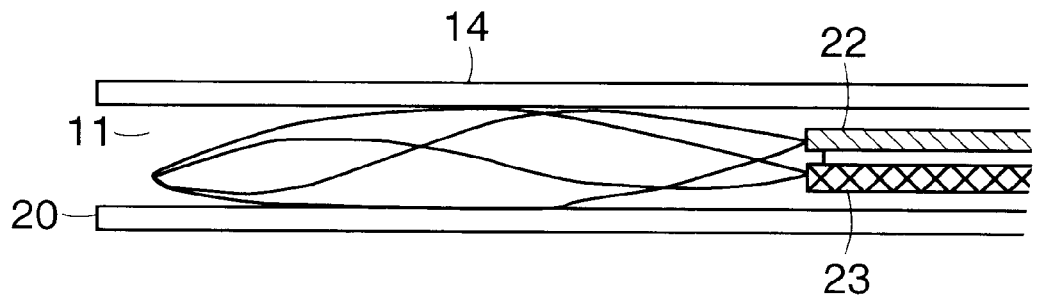
FIG. 4C shows the basket of FIG. 4A in the sheath, where the sheath defines only a single lumen therewithin.

In another embodiment, each leg may be enclosed within a single, common axially disposed lumen 11 as illustrated in FIG. 4C. In this embodiment, the entire basket may be withdrawn into the single lumen with the basket in a collapsed position, as shown.

Figure 4D:
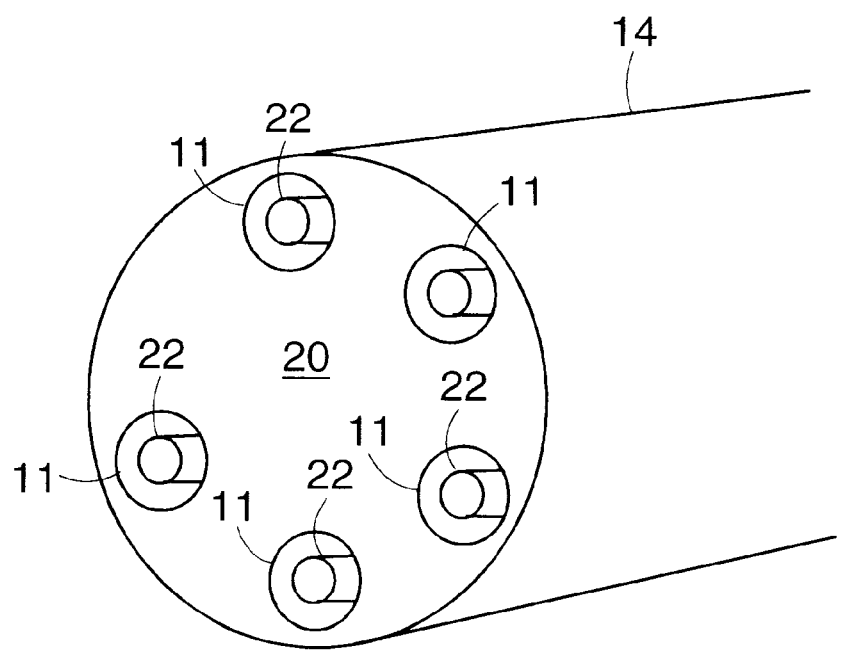
FIG. 4D is an end view of another embodiment of the invention showing a plurality of elongate members and lumens within the sheath.

In other embodiments of the invention, various ones of the legs can be attached to certain ones of the elongate members. As illustrated in FIG. 4D, there may be as many elongate members and as many lumens as there are legs. A plurality of lumens 11 are provided in the embodiment of the sheath 14 shown in FIG. 4D, and each lumen 11 is designed to accommodate a different one of the elongate members 22. Whatever the combination of legs and elongate members, the combination will result in a device 15 having a basket 10 with one or more individually actuateable legs that allow the basket to be steered, tilted, and generally maneuvered into a variety of positions and configurations beyond simple extended and collapsed, and this maneuverability or danceability allows an operator of the basket to more easily capture stones and other material with the basket legs.

Figure 5A:
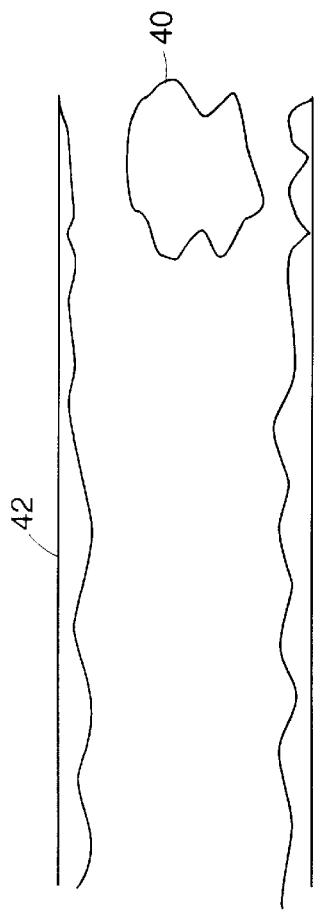
FIGS. 5A–5E are diagrammatic representations of a clinical application of one embodiment of the device illustrated in FIGS. 4A, 4B, and 4C.
Figure 5B:
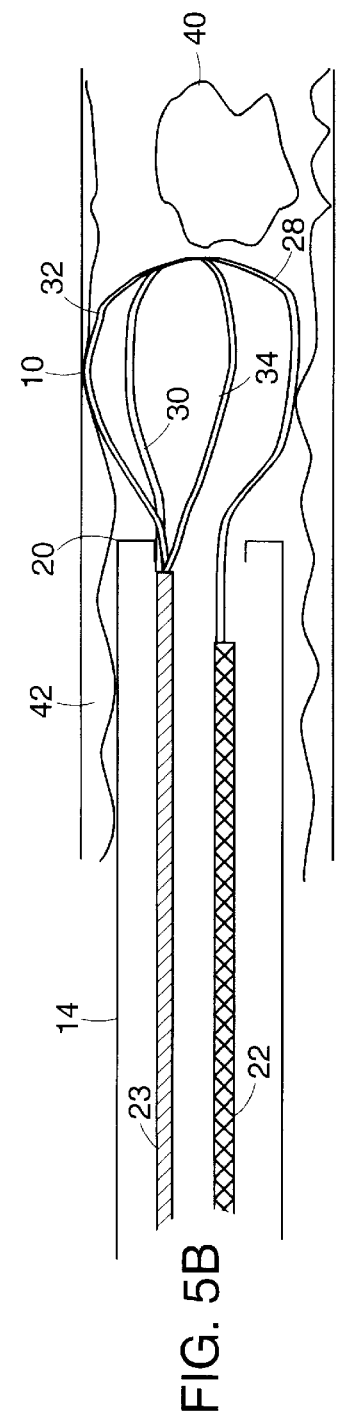
Figure 5C:
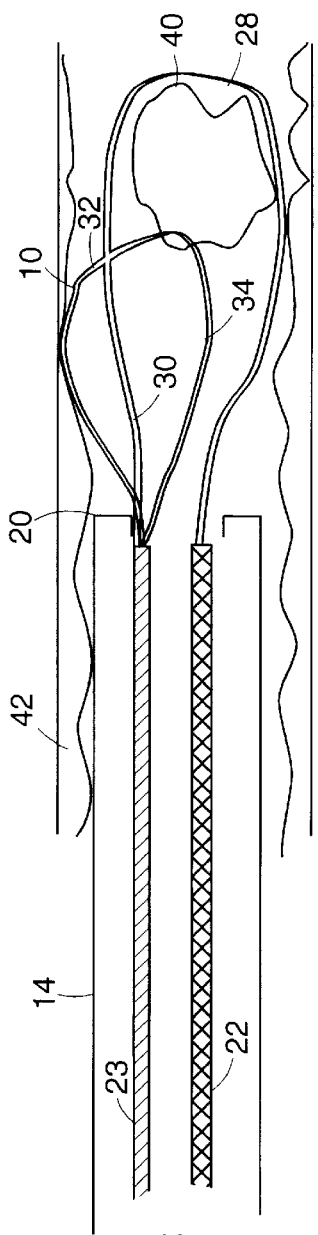
Figure 5D:
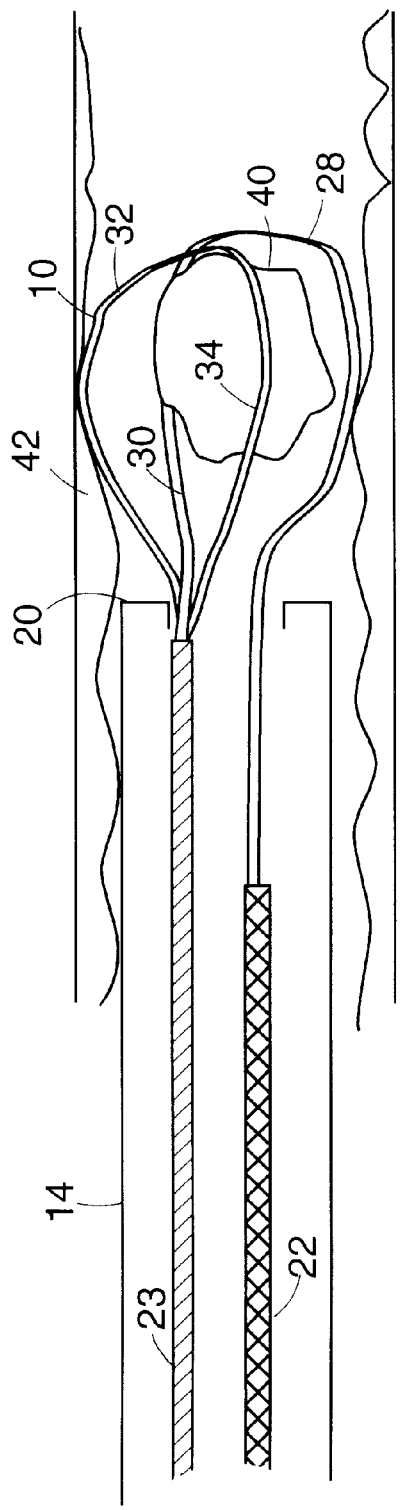
Figure 5E:
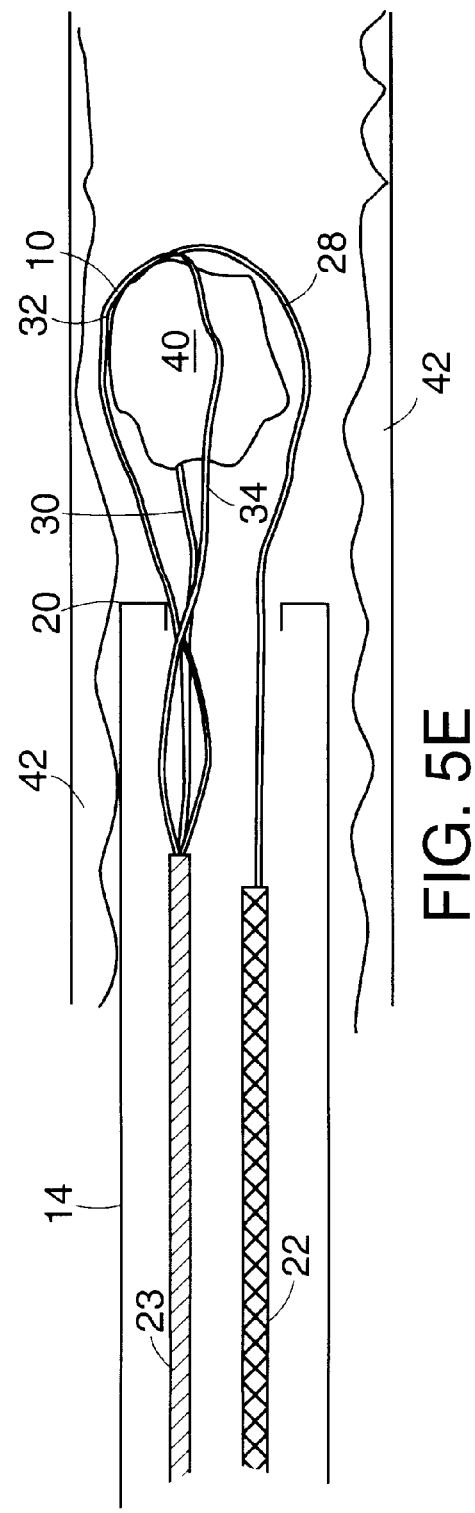

Referring to FIGS. 5A–5E, the device 15 of the invention can be used in a clinical application to retrieve biological material or foreign material from within a body. For example, the single-lumen device of FIG. 4C can be used to retrieve a stone 40 (e.g., a stone in the gall bladder, biliary tree, ureter, kidney, urinary bladder, urethra, etc.). It could also be used to capture a thrombus or embolus within a vessel such as the coronary vessels of the heart or the pulmonary vasculature. Regardless of what exactly is being retrieved, the device 15 with the basket 10 enclosed within the sheath 14 of the device is inserted into a tract 42 of the body. The tract 42 can be a canal, duct, tube, channel, vessel, or orifice of the body. As the distal end 20 of the sheath 14 approaches the stone 40 or other material, the basket 10 is deployed from the distal end 20 of the sheath 14 by advancing the slideably moveable elongate members 22 and 23 toward the distal end 20 of the sheath 14 (FIG. 5B). In another alternative embodiment, the sheath 14 may be withdrawn relative to the elongate members 22 and 23, thereby extending basket 10 from the end of the sheath 14.

After the basket is deployed to form a uniform three-dimensional basket shape (FIG. 5B) in the closed position, the single actuateable leg 28 is hyperextended by independently further advancing elongate member 22. The basket thus moves from the closed position shown in FIG. 5B to the open position illustrated in FIG. 5C. The distance between leg 28 and legs 30, 32, and 34 is thereby increased in size. The basket is thus maneuvered to ensnare the stone 40 by actuation of the leg 28. The individually-actuateable leg 28 is then withdrawn into the sheath 14 by independently retracting elongate member 22 (FIG. 5D) until the inner surface of the leg 28 and the inner surfaces of the other legs 30, 32, 34 are substantially in contact with the stone 40. The stone 40 can now be fully captured by the basket by further withdrawing the elongate members 22, 23 into the sheath 14 to draw all of the legs 28, 30, 32, 34 back towards the distal end of the sheath and around the stone 40. The device 15 with the stone 40 thus ensnared by the basket is now withdrawn from the tract 42 by the operator.

Other mechanisms for providing the individual leg actuatability in accordance with the invention are possible. Referring to FIGS. 6A–6E, the device 15 includes a slideably moveable ring 52 in the lumen 11 of sheath 14, a collar ring stop 54, a positive return ring stop 60, and a plurality of second elongate members 56, 56' operably attached to the legs 50-50' and the ring 52. Each of the basket legs 28, 28', 50, 50' are operably attached at their proximal ends 6 at the basket base 18 to the distal end 24 of a first elongate member 22 which is slideably moveable in lumen 11 of sheath 14. The second elongate member 56, 56' is operably attached at one end to the proximal portion 58, 58' of the legs 50, 50', respectively. The second elongate member 56, 56' extends longitudinally in the lumen 11 of the sheath 14 and is operably attached at its other end to the ring 52. The ring 52 encircles the first elongate member 22 within the lumen II of the sheath 14. The ring 52 is slideably moveable over the first elongate member 22 within the lumen 11. The collar ring stop 54, disposed on the inner surface of the sheath 14, stops the ring 52 from further axially advancing in the direction of the distal end 20 of the sheath 14. The positive return ring stop 60 attached to elongate member 22 is drawn into collar ring 52 as elongate member 22 is withdrawn into the lumen 11 in a direction opposite to distal end of the sheath 20.

Figure 6D:
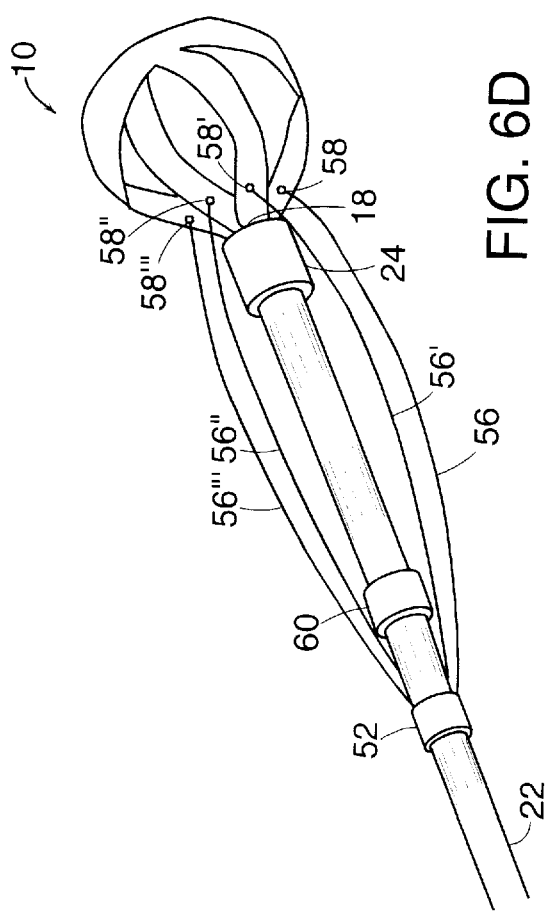
FIG. 6D shows a three-dimensional view of a basket of the invention with the sheath removed where a second elongate member is attached to each basket leg.
Figure 6E:
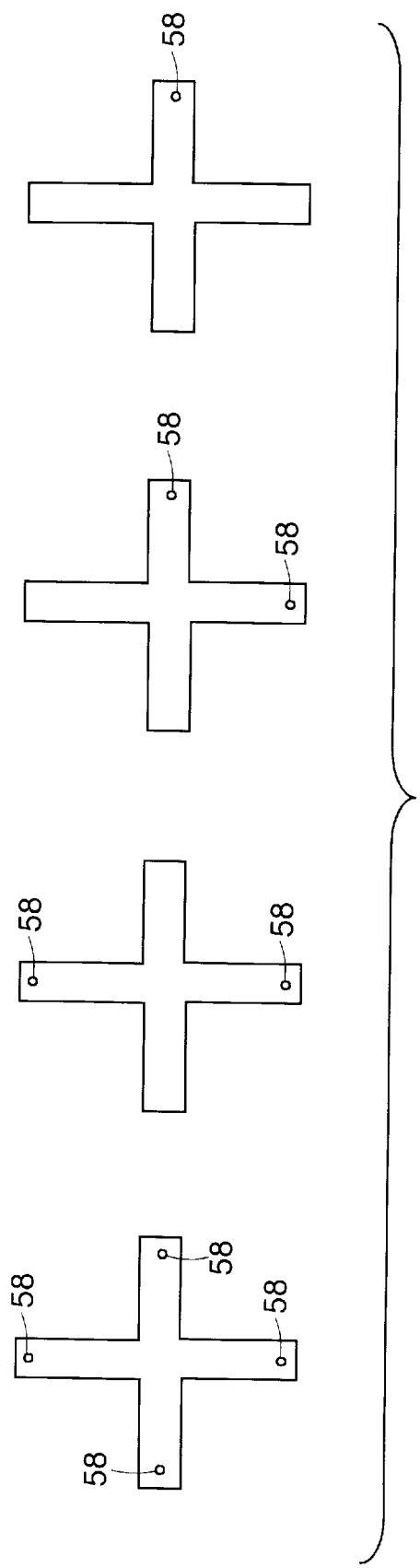
FIG. 6E is an end view of the proximal portion of the basket illustrating different arrangements for the attachment site where one or more second elongate members attach to the proximal portion of the basket legs.

In other embodiments, second elongate members may be attached to one or more of the basket legs. For example, as illustrated in FIG. 6D, second elongate members 56, 56', 56" and 56''' are attached to each of the basket legs 58, 58', 58" and 58''', respectively. FIG. 6E illustrates different arrangements of the attachment 58 of second elongate members to one or more basket legs.

In operation, as shown in FIGS. 6B and 6C, as the first elongate member 22 is axially moved in the direction of the end 20 of the sheath 14, the basket 10 is advanced out of the sheath 14, simultaneously advancing the ring 52 in the lumen 11 of the sheath 14 until the ring 52 meets the collar ring stop 54. Further advancement of the ring 52 is prevented by the collar ring stop 54. As the first elongate member 22 is further axially advanced in the lumen 11, the second elongate member 56, 56' that is attached to the ring 52 and the legs 50, 50' prevents further axial advancement of the legs 50, 50'. The legs 50, 50' thus bow out as the first elongate member 22 further advances the legs 28, 28', thereby altering the shape of the open basket such that it takes on a type of mushroom profile.

Referring again to FIG. 6A, the basket 10 is withdrawn into the sheath 14 by withdrawing elongate member 22 in a direction away from the end 20 of the sheath 14. As elongate member 22 moves in the lumen 11 of sheath 14, positive ring stop 60 strikes collar ring 52. When positive ring stop 58 strikes collar ring 52, positive ring stop 60 moves collar ring 52 along with and in the same direction as elongate member 22 as elongate member 52 is withdrawn into the lumen 11 of the sheath 14.

In all embodiments according to the invention, the basket provides a dilatation force unachievable with traditional baskets. This is due to the extra force supplied by a user in moving one or more of the legs further than possible with known baskets. The extra force supplied by the operator's hand gives rise to the basket's ability to provide an improved expansion force.

In another aspect of the invention, all or a part of the inner surface of one or more of the basket legs can be rough to enhance capture and retention of material such as stones and possibly also to crush or break material. The roughness of the inner surface(s) can be created by serrations, etching, teeth, or points on or in the inner surface(s). One or more of the basket legs can have such a rough inner surface.

Variations, modifications, and other implementations of what is described herein will occur to those of ordinary skill in the art without departing from the spirit and the scope of the invention as claimed. Accordingly, the invention is to be defined not by the preceding description but instead by the spirit and scope following claims.

What is claimed is:

1. A medical retrieval device, comprising:
   a proximal handle;
   a sheath extending from the handle and including a lumen, the sheath having a distal end away from the handle;
   at least one elongated member;
   a basket comprising a distal end and a base, the basket and the sheath moveable relative to each other to achieve a collapsed position of the basket in which the basket is within the lumen of the sheath and restrained by said sheath; and an extended position of the basket in which the basket extends from the distal end of the sheath and assumes a three-dimensional shape out of the lumen of the sheath, the basket comprising at least three legs joined at their distal end to a distal end of the basket, each leg fixedly attached to at least one elongated member, at least one of the legs being moveable within the lumen of said sheath independently from at least one of the other legs.

2. The device of claim 1 wherein at least one of the legs is coupled to a first elongate member extending within the lumen of the sheath to the handle, and wherein at least one other different one of the legs is coupled to a second elongate member extending within the lumen of the sheath to the handle, such that independent movement of the first elongate member within the sheath causes independent movement of the leg coupled thereto and independent movement of the second elongate member within the sheath causes independent movement of the leg coupled thereto.

3. The device of claim 1 wherein at least one of the legs includes an inner surface which has at least a portion that is rough.

4. The device of claim 1 wherein the distal end of the basket is non-perforated.

5. A medical retrieval device, comprising:
   a proximal handle;
   a sheath extending from the handle and including at least one lumen, the sheath having a distal end away from the handle;
   a basket, said basket and sheath moveable relative to each other to achieve a collapsed position of the basket in which the basket is within the lumen of the sheath and an extended position of the basket in which the basket extends from the distal end of the sheath and assumes a three-dimensional shape out of the lumen of the sheath, the basket comprising a base, a distal end, and at least three legs joined at the distal end of the basket;
   a first elongate member disposed and moveable within the lumen of the sheath and attached at one end to the base of the basket;
   a ring encircling the first elongate member and disposed and moveable within the lumen of the sheath;
   a second elongate member moveable within the lumen of the sheath and attached at one end to the ring and at the other end to at least one of the legs; and
   a stop within the lumen of the sheath for contact by the ring to prevent the second elongate member from advancing beyond a predetermined distance within the lumen such that further movement by the first elongate member within the lumen toward the distal end of the sheath causes the shape of the basket to become altered.

6. A medical retrieval device, comprising:
   a proximal handle;
   a sheath extending from the handle and including a plurality of lumens, the sheath having a distal end away from the handle; and
   a basket moveable between a collapsed position and an extended position, the basket comprising at least three legs joined at the distal end of the basket, each leg disposed and moveable within a different one of the lumens, and at least one of the legs being moveable independently from at least one of the other legs, the basket taking a three-dimensional shape when all legs are extended out of the distal end of the sheath, the basket having a distal end which is non-perforated.

7. The device of claim 6 further comprising at least two elongate members wherein at least one of the legs is coupled to a different one of the at least two elongate members than at least one of the other legs, each elongate member disposed and moveable within a different lumen, and wherein at least one of the elongate members is moveable independently from at least one of the other elongate members, such that independent movement of at least one of the elongate members within the sheath causes independent movement of the at least one leg coupled thereto.

8. The device of claim 6 wherein at least one of the legs includes an inner surface which has at least a portion that is rough.

9. A method for retrieving material from a body, comprising:
   inserting a medical retrieval device into a body, the device comprising a basket comprising a distal end and a base, a proximal handle, and a sheath extending from the handle and including at least one lumen, the sheath having a distal end away from the handle, at least one elongated member, said basket and said sheath moveable relative to each other to achieve a collapsed position of the basket in which the basket is within the lumen of the sheath and restrained by said sheath, and an extended position of the basket in which the basket extends from the distal end of the sheath and assumes a three-dimensional shape out of the lumen of the sheath, the basket comprising at least three legs joined at their distal end to the distal end of the basket, each leg fixedly attached to at least one elongated member at least one of the legs being moveable within the lumen of said sheath-independently from at least one of the other legs;

placing the basket in the extended position;

maneuvering the basket to surround the material by moving at least one of the legs independently from at least one of the other legs;

drawing all of the legs back into the lumen to grasp the material with the legs of the basket; and withdrawing the device from the body to remove the grasped material from the body.

* * * * *